United States Patent [19]

Black

[11] 4,267,325
[45] May 12, 1981

[54] BLEACHING AGENTS

[75] Inventor: Robin M. Black, Porton, near Salisbury, England

[73] Assignee: Cadbury-Schweppes Limited, London, England

[21] Appl. No.: 15,705

[22] Filed: Feb. 27, 1979

[51] Int. Cl.$^3$ ................ C07D 239/80; C07D 241/52; C07D 235/26
[52] U.S. Cl. ...................... 544/285; 252/95; 544/354; 548/305
[58] Field of Search ............... 544/285, 354; 548/305

[56] References Cited

U.S. PATENT DOCUMENTS 3,007,876  11/1961  Schaeffer ........................ 544/285
3,326,915  6/1967   Jackson et al. .................. 544/354

FOREIGN PATENT DOCUMENTS 847566  9/1960  United Kingdom ................. 544/285

Primary Examiner—Donald G. Daus
Assistant Examiner—James H. Turnipseed
Attorney, Agent, or Firm—Ostrolenk, Faber, Gerb & Soffen

[57] ABSTRACT

N-chlorinated sulphonic acids of the formula

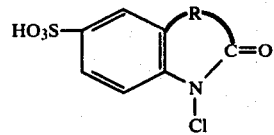

(wherein R is group

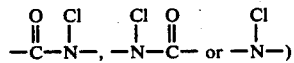

and their salts, particularly their sodium and potassium salts, are disclosed. These compounds are chlorine release agents and may be used as bleaching or germicidal agents either alone or in cleansing or detergent compositions. Preferred compounds are those wherein R is a group

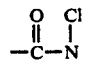

in the form of their sodium or potassium salts.

8 Claims, No Drawings

BLEACHING AGENTS

This invention is concerned with solid N-chlorinated organic compounds, the preparation thereof, and compositions containing them. The invention is particularly concerned with solid N-chlorinated organic compounds suitable for use as germicides, bleaching agents and chlorinating agents, i.e. compounds which may be used as so-called "chlorine release agents" in, for example, detergent and/or disinfectant compositions. A variety of N-chlorinated compounds have been proposed for use as chlorine release agents such as, for example, N,N'-dichlorobenzoylene-urea which is a stable and efficient bleaching agent but which has a very low water solubility.

It has now been found, in accordance with the present invention, that certain N-chlorinated organic compounds, as hereinafter defined, are generally stable solid compounds having an appreciable water solubility.

Accordingly, the present invention provides, as new compounds, N-chlorinated sulphonic acids of the general formula:

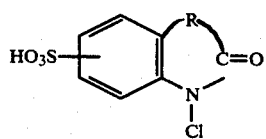
(I)

in which R is a group

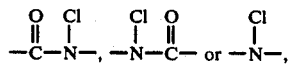

and salts thereof, especially alkali metal salts thereof such as sodium or potassium salts.

Preferred compounds in accordance with the invention are compounds in which R is a group

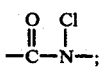

i.e. 1,3-dichloro-1,2,3,4-tetrahydro-2, 4-dioxoquinazoline-6-sulphonic acid derivatives of the formula:

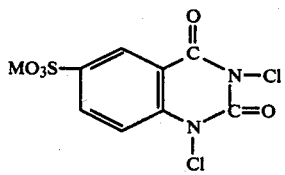
(II)

in which M is a sodium or potassium atom.

The new compounds of the invention may be prepared by chlorinating an appropriate sulphonic acid of the formula:

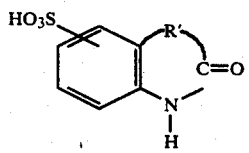
(III)

or salt thereof, in which R¹ represents a group

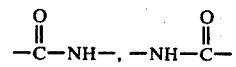

or —NH—. Such chlorination is conveniently effected by passing chlorine into a cooled aqueous solution of the appropriate acid in the presence of excess alkali, e.g. sodium hydroxide, sodium carbonate, potassium hydroxide or potassium carbonate. Alternatively, the chlorination may be effected by passing chlorine into an aqueous solution of the sodium or potassium salt of the sulphonic acid in the presence of excess sodium or potassium acetate or bicarbonate to neutralize the hydrochloric acid formed. This latter process is preferred for the preparation of compounds wherein R is a group

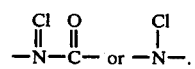

The starting sulphonic acids of the formula:

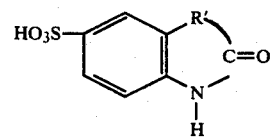

may be prepared by sulphonating an appropriate unsubstituted compound of the formula:

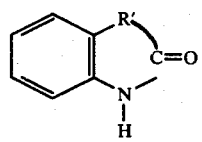
(IV)

with a mixture of sulphuric acid and fuming sulphuric acid. Alternatively, the sulphonic acids of formula III may be prepared by well-known cyclization reactions from substituted benzene sulphonic acids of the formula:

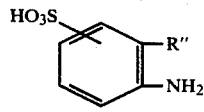

in which R" is an amino or carboxy group (See Japanese Patent No. 26,974; Chem. Abst. 62,11833; German Offenlegungsschrift No. 2,131,367; Chem. Abst. 78,84413). Thus, quinazoline-2,4-diones are generally synthesised by treating anthranilic acids with cyanic acid and cyclising the resulting urea with base, or the anthranilic acids may be fused with urea. Quinoxaline-2,3-diones are synthesised by heating o-phenylenediamines with oxalic acid or alkyl oxalate. Benzimidazolones are formed from o-phenylenediamines by treatment with phosgene or heating with urea.

The active chlorine containing compounds of the invention are stable solids which dissolve in water to release active chlorine and the resultant solutions can be used for bleaching, disinfecting and sterilizing operations. The compounds of the invention maybe used per se for addition to water to give such solutions in which case they may be formulated, for example, in tablet form optionally with inert tabletting ingredients. Alternatively, the new compounds may be formulated with other active ingredients such as surface active agents, water-softening agents, builders such as alkali metal polyphosphates or sequestering agents to give detergent or cleansing compositions also having a bleaching or disinfectant activity.

In order that the invention may be well understood the following Examples are given by way of illustration only.

EXAMPLE 1

1,2,3,4-Tetrahydro-2,4-dioxoquinazoline-6-sulphonic acid 2,4(1H, 3H)-Quinazolinedione (10 g) was added portionwise to a stirred mixture of 65% fuming sulphuric acid (10 ml) and concentrated sulphuric acid (40 ml) at room temperature. After the addition was complete, the mixture was stirred at 55°–60° for 30 minutes, cooled, poured onto ice (100 g) and stood in a refrigerator for 1 hour. The colourless crystals were filtered, washed with a little ice-cold 6 N hydrochloric acid and finally dried in a vacuum oven to give the hydrated title compound, (14.7 g, m.p. >300°).

EXAMPLE 2

1,3-Dichloro-1,2,3,4-tetrahydro-2,4-dioxoquinazoline-6-sulphonic acid sodium salt (a) Chlorine was passed rapidly for 5 minutes and slowly for 15 minutes into a vigorously stirred ice-cooled solution of 1,2,3,4-tetrahydro-2,4-dioxoquinazoline-6-sulphonic acid (10.4 g) and sodium hydroxide (9.6 g) in water (240 ml) at ca. 8°. The white precipitate was filtered, washed with a little ice-cold water, then ethyl acetate and dried under vacuum over $P_2O_5$ (10.1 g).

Active chlorine content 37.8% (theoretical 42.6%).

Recrystallisation from hot water yielded a purer sample as white needles (6.3 g).

Active chlorine content 42.1%.

(b) Chlorine was passed rapidly for 5 minutes and slowly for 15 minutes into a vigorously stirred ice-cooled suspension of 1,2,3,4-tetrahydro-2,4-dioxoquinazoline-6-sulphonic acid, sodium salt [from the acid (10.4 g) and sodium hydroxide] and sodium acetate (10 g) in water (250 ml) at ca. 10°. Work-up as in example 2(a) gave the title compound as a white solid (10.0 g).

Active chlorine content 37.1%.

EXAMPLE 3

1,3-Dichloro-1,2,3,4-tetrahydro-2,4-dioxoquinazoline-6-sulphonic acid, potassium salt Chlorine was passed rapidly for 5 minutes and slowly for 10 minutes into a vigorously stirred ice-cooled solution of 1,2,3,4-tetrahydro-2,4-dioxoquinazoline-6-sulphonic acid (10.4 g) and potassium hydroxide (13.4 g) in water (240 ml) at ca. 6°. The white precipitate was filtered, washed with a little ice-cold water, then ethyl acetate and vacuum dried over $P_2O_5$ at ca. 40° (13.2 g).

Active chlorine content 36.5% (theoretical 40.6%).

Recrystallisation from hot water yielded colourless needles (8.85 g).

Active chlorine content 30.6%.

EXAMPLE 4

1,2,3,4-Tetrahydro-2,3-dioxoquinoxaline-6-sulphonic acid 2,3(1H, 4H)-Quinoxalinedione (10 g) was added portionwise to a stirred mixture of 65% fuming sulphuric acid (10 ml) and conc. sulphuric acid (40 ml) at room temperature. After stirring for 30 minutes at 55°–60°, the mixture was worked up as in example 1 to give the hydrated crystalline product (15.3 g, mp. >300°).

EXAMPLE 5

1,4-Dichloro-1,2,3,4-tetrahydro-2,3-dioxoquinoxaline-6-sulphonic acid, sodium salt Chlorine was passed rapidly for 5 minutes and slowly for 15 minutes into a vigorously stirred ice-cooled suspension of 1,2,3,4-tetrahydro-2,3-dioxoquinoxaline-6-sulphonic acid sodium salt [from the acid (2.6 g) neutralised with sodium hydroxide] and sodium acetate (4 g) in water (60 ml) at ca. 8°. The yellowish precipitate was filtered, washed with ice-cold water and ethyl acetate, and vacuum dried to give a slightly yellowish solid (2.80 g).

Active chlorine content 38.3% (theoretical 42.6%).

Recrystallisation from hot water gave a sample as almost white needles.

Active chlorine content 41.8%.

EXAMPLE 6

1,4-Dichloro-1,2,3,4-tetrahydro-2,3-dioxoquinoxaline-6-sulphonic acid, potassium salt Chlorine was passed rapidly for 3 minutes and slowly for 15 minutes into a stirred suspension of 1,2,3,4-tetrahydro-2,3-dioxoquinoxaline-6-sulphonic acid potassium salt [from the acid (2.6 g) neutralised with potassium hydroxide] and potassium acetate (4 g) in water (60 ml) at ca. 8°. Work-up as in Example 5 gave the product as a slightly yellowing solid (2.48 g).

Active chlorine content 36.7% (theoretical 40.6%).

EXAMPLE 7

2,3-Dihydro-(1H)-2-oxobenzimidazole-5-sulphonic acid

2(3H)-Benzimidazolone (10 g) was added portionwise to a stirred mixture of 65% fuming sulphuric acid (10 ml) and conc. sulphuric acid (40 ml) at room temperature, and the mixture then stirred for 30 minutes at 55°–60°. Work-up as in Example 1 gave the title compound as colourless crystals (34.7 g, m.p. >300°).

EXAMPLE 8

1,3-Dichloro-2,3-dihydro-(1H)-2-oxobenzimidazole-5-sulphonic acid, sodium salt

Chlorine was passed rapidly for 5 minutes and slowly for 10 minutes into a vigorously stirred ice-cooled suspension of 2,3-dihydro-(1H)-2-oxobenzimidazole-5-sulphonic acid sodium salt [from the acid (4.28 g) neutralised with sodium hydroxide] and sodium acetate (8.0 g) in water (100 ml) at ca. 6°. Work-up as in Example 5 gave a white solid (4.2 g).

Active chlorine content 42.1% (theoretical 46.2%).

EXAMPLE 9

1,2,3,4-Tetrahydro-2,4-dioxoquinazoline-7-sulphonic acid, sodium salt

A solution of potassium cyanate (5.5 g) in water (25 ml) was added dropwise to a stirred solution of 3-amino-4-carboxybenesulphonic acid (10.85 g) [for preparation see Chem. Abstr. 56, 7195] in water (250 ml), adjusted to ca. pH 5 with sodium hydroxide solution, and glacial acetic acid (5 ml). After stirring for 1 hour at room temperature, a saturated aqueous solution of sodium hydroxide (60 g) was added with cooling, and the mixture stirred for a further 30 minutes. The mixture was cooled in an ice bath and acidified with 18 N sulphuric acid (90 ml). The precipitate was filtered and recrystallised from water (ca. 200 ml), to yield the title compound as white crystals (9.5 g), m.p. >350°.

EXAMPLE 10

1,3-Dichloro-1,2,3,4-tetrahydro-2,4-dioxoquinazoline-7-sulphonic acid, sodium salt Chlorine was passed rapidly for five minutes and slowly for twenty minutes into a rapidly stirred suspension of 1,2,3,4-tetrahydro-2,4-dioxoquinazoline-7-sulphonic acid, sodium salt (2.64 g) and sodium acetate (4 g) in water (50 ml) at ca. 8°. The yellowish precipitate was filtered, washed with ice-cold water, then ethyl acetate and vacuum dried over P$_2$O$_5$ to give the title compound (2.25 g) as a white solid.

Active chlorine content 39.7% (theoretical 42.6%).

I claim:

1. N-Chlorinated sulphonic acids of the formula:

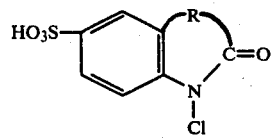

and alkali metal salts thereof, wherein R is a group selected from the group consisting of groups of the formula:

$$-\overset{O}{\underset{\|}{C}}-\overset{Cl}{\underset{|}{N}}-,$$

$$-\overset{Cl}{\underset{|}{N}}-\overset{O}{\underset{\|}{C}}-, \text{ and}$$

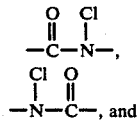

2. Alkali metal N-chlorinated sulphonates of the formula:

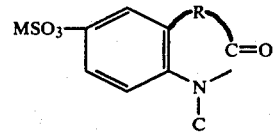

wherein R is a group selected from the group consisting of groups of the formulae:

$$-\overset{O}{\underset{\|}{C}}-\overset{Cl}{\underset{|}{N}}-,$$

$$-\overset{Cl}{\underset{|}{N}}-\overset{O}{\underset{\|}{C}}-, \text{ and}$$

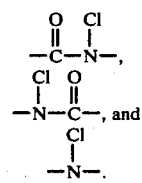

and M is sodium or potassium.

3. Alkali metal N-chlorinated sulphonates of the formula:

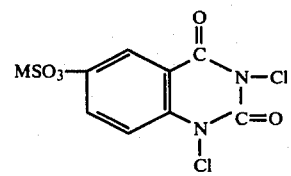

wherein M is sodium or potassium.

4. 1,3-Dichloro-1,2,3,4-tetrahydro-2,4-dioxoquinazoline-6-sulphonic acid in accordance with claim 1.

5. 1,3-Dichloro-1,2,3,4-tetrahydro-2,4-dioxoquinazoline-6-sulphonic acid, sodium or potassium salt in accordance with claim 3.

6. 1,3-Dichloro-1,2,3,4-tetrahydro-2,3-dioxoquinoxaline-6-sulphonic acid and the sodium and potassium salts thereof in accordance with claim 1.

7. 1,3-Dichloro-2,3-dihydro-(1H)-2-oxobenzimidazole-5-sulphonic acid and the sodium salt thereof in accordance with claim 1.

8. 1,3-Dichloro-1,2,3,4-tetrahydro-2,4-dioxoquinazoline-7-sulphonic acid and the sodium salt thereof in accordance with claim 1.

* * * * *